United States Patent
Passalaqua et al.

[11] Patent Number: 6,007,526
[45] Date of Patent: *Dec. 28, 1999

[54] MALE EXTERNAL CATHETER WITH SHORT ANNULAR SEALING FLAP

[75] Inventors: James J. Passalaqua, Paddock Lake, Wis.; Dustin T. Lyle, Grays Lake, Ill.; Susan C. Gorski, Mundelein, Ill.; Teri G. Johnston, Crystal Lake, Ill.; Michael A. Metz, Chicago, Ill.

[73] Assignee: Hollister Incorporated, Libertyville, Ill.

[*] Notice: Under 35 U.S.C. 154(b), the term of this patent shall be extended for 247 days.

[21] Appl. No.: 08/542,180

[22] Filed: Oct. 12, 1995

[51] Int. Cl.⁶ .................................................. A61F 5/44
[52] U.S. Cl. ........................ 604/349; 604/352; 128/844
[58] Field of Search .................... 604/349, 352, 604/346, 347; 128/842, 843, 844; 602/58, 901

[56] References Cited

U.S. PATENT DOCUMENTS

| | | | |
|---|---|---|---|
| Re. 33,206 | 5/1990 | Conway et al. | 604/349 |
| D. 358,882 | 5/1995 | Metz et al. | D24/112 |
| 4,540,409 | 9/1985 | Nystrom et al. | 604/349 |
| 4,581,026 | 4/1986 | Schneider | 604/352 |
| 4,586,974 | 5/1986 | Nystrom et al. | 156/165 |
| 4,589,874 | 5/1986 | Riedel et al. | 604/349 |
| 4,626,250 | 12/1986 | Schneider | 604/352 |
| 4,932,948 | 6/1990 | Kernes et al. | 604/349 |
| 5,336,211 | 8/1994 | Metz | 604/349 |
| 5,423,784 | 6/1995 | Metz | 604/349 |

FOREIGN PATENT DOCUMENTS

| | | |
|---|---|---|
| 2099706 | 6/1981 | United Kingdom . |
| 2198952 | 12/1986 | United Kingdom . |

*Primary Examiner*—Corrine McDermott
*Assistant Examiner*—David J. Cho
*Attorney, Agent, or Firm*—Tilton Fallon Lungmus

[57] ABSTRACT

An external catheter for a male urinary incontinence collection system is disclosed, the catheter taking the form of a tubular sheath of soft elastic material having a thin-walled cylindrical section, a reduced drainage tube section, and an intermediate section merging with both the drainage tube and cylindrical sections. The sheath also includes a thin elastic annular flap extending inwardly from the sheath's inner surface where the intermediate and cylindrical sections merge. The flap has an inner end defining a generally circular opening of a critical size in relation to the inside diameter of cylindrical section and the length of the intermediate section.

4 Claims, 2 Drawing Sheets

MALE EXTERNAL CATHETER WITH SHORT ANNULAR SEALING FLAP

BACKGROUND AND SUMMARY

Co-owned Pat. Nos. 4,581,026, 4,626,250, and 4,932,948 disclose male external catheters intended for use with urinary drainage systems. Each such catheter is in the form of a sheath having a cylindrical body section, an intermediate neck section, and a reduced drainage tube section, with the entire catheter being formed of a soft elastic material such as latex or silicone rubber. In addition, the catheters disclosed in each of these patents have tubular elongated inner sleeves of soft elastic material designed to fit over the glans of a wearer's penis. Such a sleeve is intended to make sealing contact with the glans and is maintained in stretched condition over the glans by adhesive means adhering the cylindrical section to the penile shaft.

As shown in these patents, the tubular sleeves are relatively long, so as to cover as much of the glans as possible, and terminate in small distal openings so that urine may be discharged into the intermediate neck portions of the sheaths. For sealing effectiveness, it has been considered important to insure that the thin elastic sleeves are stretched over the glans and are maintained in such stretched condition when the catheters are worn. That requires the caregiver or the patient (if a catheter is self-applied) to hold the penis in position as the sleeve is stretched over the glans. While devices have been developed to make the task easier (see, for example, the applicator of co-owned Pat. No. 4,589,874), it is still necessary for the user to use both hands in the application of such a catheter, one for unrolling the sheath over the penis and the other for holding the penis, with the sleeve in stretched condition over the glans, at least at the commencement of that operation.

While an adhesively-attached catheter with an inner sleeve operates effectively if it is applied carefully with the sleeve stretched over the glans, instances have occurred where nurses (or other caregivers) have failed to perform such procedures completely, or with sufficient patience and care, because they are concerned about possible discomfort or injury to the patient, or are rushing to perform other healthcare duties, or simply because they find themselves uncomfortable making such direct and extended contact with the limp penis of an incontinent patient. If such an external catheter is improperly or incompletely applied, it may cause considerable patient discomfort and produce other serious consequences such as rendering the device ineffective or inoperative and causing leakage of urine when the drainage system is in use.

Other problems may also arise. If the stretched inner sleeve is to cover the glans, it is important that it be relatively long and that its distal opening be small. However, such a device obviously will fail to operate properly if the small distal opening of the stretched sleeve is not in register with the urethral opening of the patient, so care must be taken to assure that proper alignment exists. Also, in fitting such a sheath upon a patient, it is important that the sleeve be stretched, but not stretched excessively, because excessive stretching might cause the distal end of the sleeve to be positioned near the backside of the glans, or even behind the glans, applying a clearly undesirable constrictive force on the patient.

Recent developments in catheter-applying techniques involve the use of catheters that are similar to those described above but may or may not supplied or applied in rolled form and may or may not have inner sleeves. Reference may be had to co-owned Pat. Nos. 5,423,784, 5,336, 211, 4,586,974, 4,540,409, and Des. No. 358,882. In each, a catheter is supported by an open-ended applicator tube with the neck and drainage tube portions of the catheter located within the tube and the cylindrical portion of the catheter reverted or turned backwardly over the outside of the tube. Such a system generally allows the user to apply a catheter to a patient without gripping the penis between the fingers, but some gripping may still be necessary if the catheter has an inner sleeve that should be stretched over the glans during application. In such a case, the ease of application may be decreased rather than increased because operation of the applicator tube in releasing and applying a catheter is itself a two-handed operation, making it difficult for the user to also hold the penis and stretch the sleeve over the glans.

An important aspect of this invention therefore lies in the discovery that the advantages of sleeve-equipped catheter may be realized without encountering the difficulties indicated above if such a sleeve is shortened, its opening is greatly enlarged, and it is positioned so that it may make sealing contact with the penile shaft rather than the glans. Unlike the inner sleeves of the catheters disclosed in the aforementioned patents, the sleeve of the present catheter must be relatively short, taking the form of a narrow annular flap, and its opening must be relatively large. Specifically, the opening must be large enough so that the annular flap slides easily over the glans (or the foreskin covering the glans in an uncircumcised patient) and will sealingly engage the penile shaft or the proximal portion of the glans (or foreskin) immediately adjacent the shaft. The flap should be dimensioned so that its opening has a diameter in the general range of 75 to 92% of the inside diameter of the cylindrical portion of the sheath, with the preferred range being 78 to 89% and the optimum range being about 81 to 87%. The length of the flap depends partly on the size of the catheter but, in general, the flap should have a length within the range of about 0.25 to 0.65 inches and should not in any case exceed 35% of the length of the sheath's intermediate section. A flap length of 0.5 inches has been found particularly effective for adult-size catheters, whereas 0.3 inches has been found suitable for a pediatric-size catheter.

Other features, objects and advantages will become apparent from the specification and drawings.

DRAWINGS

DETAILED DESCRIPTION OF PREFERRED EMBODIMENTS

Figure 2:
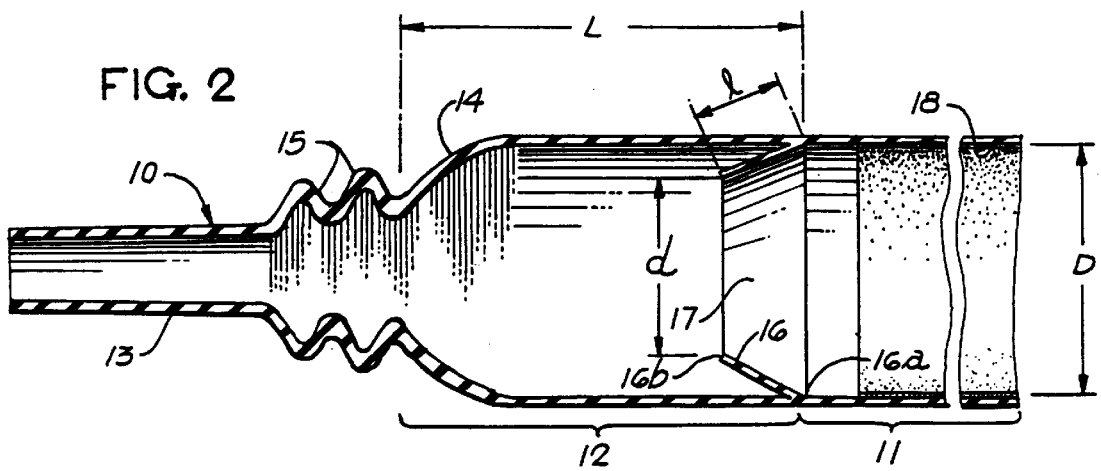
FIG. 2 is a sectional view of the catheter in extended condition.

Referring to FIG. 2 of the drawings, the numeral 10 generally designates a catheter in the form of a thin, unitary sheath of soft elastic material such as, for example, latex or silicone rubber. The sheath includes a generally cylindrical body portion 11, an intermediate portion 12, and a drainage tube portion 13. At its forward or distal end, the intermediate portion 12 is provided with a rounded taper 14 that merges with the drainage tube portion 13. Convolutions or annular enlargements 15 may be provided in the drainage tube portion at its proximal end, the purpose of such convolutions being to permit greater stretchability, bending, and twisting of the drainage tube portion when the device is in use, and to do so with less chance that kinking or obstruction of the lumen might occur. The catheter is conventionally produced by dipping and curing steps in which a mandrel of selected configuration is alternately lowered into and removed from a liquid bath of latex (or other suitable elastomer), with the wall thickness of the intermediate portion 12 and the drainage tube portion 13 being substantially thicker than the wall of cylindrical portion 11.

Figure 1:
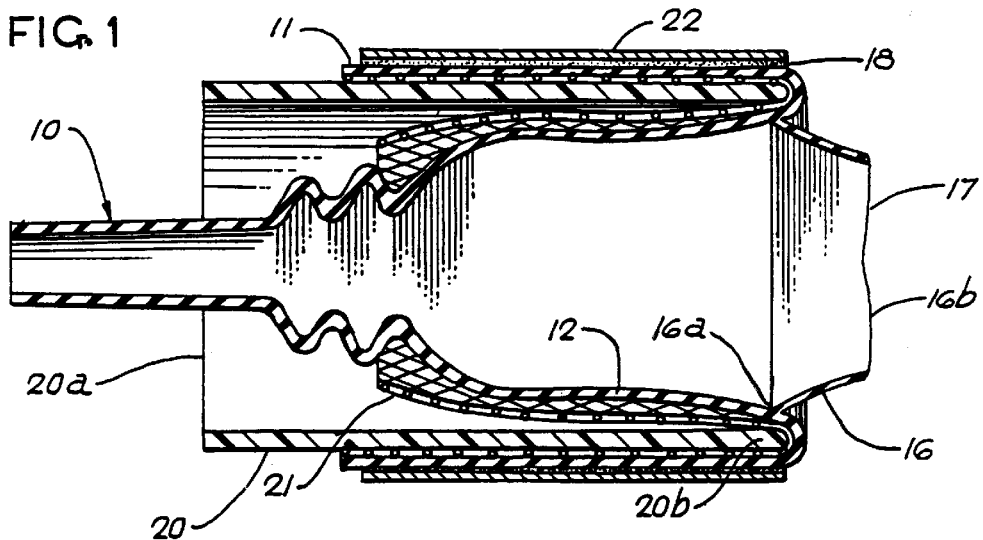
FIG. 1 is a vertical longitudinal sectional view of a catheter embodying the invention in combination with an applicator tube.

The sheath also includes an annular flap 16 located within the interior of the sheath. The flap has an outer end (determined radially) 16a that merges with the inner surface of the sheath at a point (or line) between cylindrical portion 11 and intermediate portion 12. The opposite inner end 16b of the flap defines an opening 17 slightly smaller than the interior of the cylindrical portion and intermediate portion of the sheath. In FIG. 2, the flap is shown as sloping forwardly or distally but, if desired, the flap may slope in a proximal direction or even extend radially inwardly in a plane normal to the axis of the sheath. Even when the sheath has its flap normally sloping distally, as shown in FIG. 2, that flap may tend to reverse its direction when the sheath is tensioned slightly and mounted upon an applicator tube (FIG. 1).

Like the cylindrical portion 11, the flap 16 should be extremely thin and elastically stretchable. A thickness of about 0.008 inches has been found effective for both the flap and the cylindrical wall, but greater or lesser thicknesses may be provided, if desired.

There is a critical size relationship between the opening of flap 16 and the inside diameter of the cylindrical portion 11 if effective sealing and safe operation of the catheter are to be achieved. The diameter "d" of opening 17 should generally fall within the range of 75 to 92% of the inside diameter "D" of the cylindrical body portion 11 when the sheath is in unstretched or untensioned condition. The preferred percentage ratio is 78 to 89%, with the optimum falling within the range of about 81 to 87%. The length "l" of the flap—that is, the distance between ends 16a and 16b—should be no greater than 35% of the length "L" of the intermediate portion 12 and, in general, should be within the range of about 0.25 to 0.65 inches. For adult-size catheters, the optimum is believed to be about 0.50 inches, whereas for pediatric catheters a dimension of about 0.30 inches is preferred.

The d/D ratio is critical because the flap 16 of catheter 10 must be capable of sliding over the glans of the penis (or the foreskin-covered glans for an uncircumcised male) with only limited stretching and, therefore, limited resistance. For any given patient the proper size of a catheter as a whole is primarily determined by dimension D. Ideally, the cylindrical body portion 11 of the catheter should have approximately the same diameter (inside), or a slightly smaller diameter, as that of the patient's penis in a flaccid state so that when the sheath is fitted upon the patient, adhesive layer 18 will contact the penile shaft without gaps, wrinkles, or channels that might cause leakage. Therefore, while catheters of the type depicted in FIG. 2 would be available in several different sizes, once such a catheter of proper size is selected for a given patient, based on dimension D, the flap opening 17 will also be of the proper size if the catheter embodies d/D ratios given above.

The adhesive layer 18 along the inner surface of cylindrical body portion 11 may be of any suitable medical-grade pressure sensitive adhesive. A conventional medical-grade acrylic adhesive has been found effective, but other known adhesives may be used.

FIG. 1 depicts catheter 10 supported upon an applicator tube 20. The tube is open-ended and the intermediate portion of the catheter is located within the interior of the tube with the reduced drainage tube portion 13 projecting from one end 20a. The cylindrical portion 11 of the catheter extends out of the opening at the opposite end 20b of the tube and is folded backwardly over the outside of the tube. To reduce friction between the catheter and the surfaces along the outside and end 20b of the tube 20, a mesh sleeve 21 of nylon, polyethylene, polypropylene, or some other suitable polymeric material is interposed between the two. The adhesive layer 18, on what will become the inner surface of the catheter when the cylindrical section is reverted, is covered by a removable strip of silicone-coated paper tape 22 or other suitable release covering.

Figure 4:
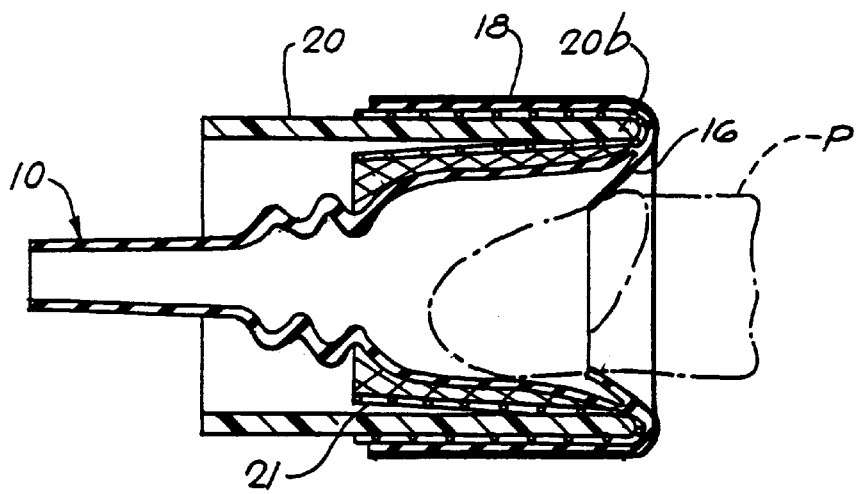
FIGS. 4–6 are longitudinal sectional views illustrating steps in the application of the catheter to a patient.
Figure 5:
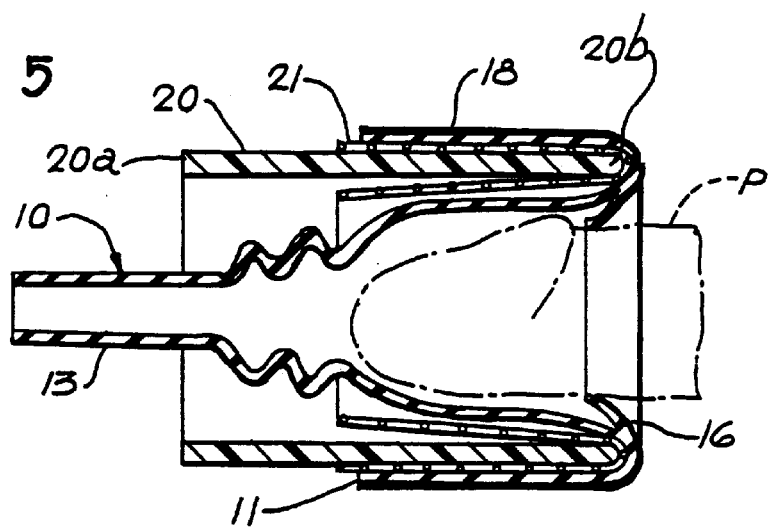
Figure 6:
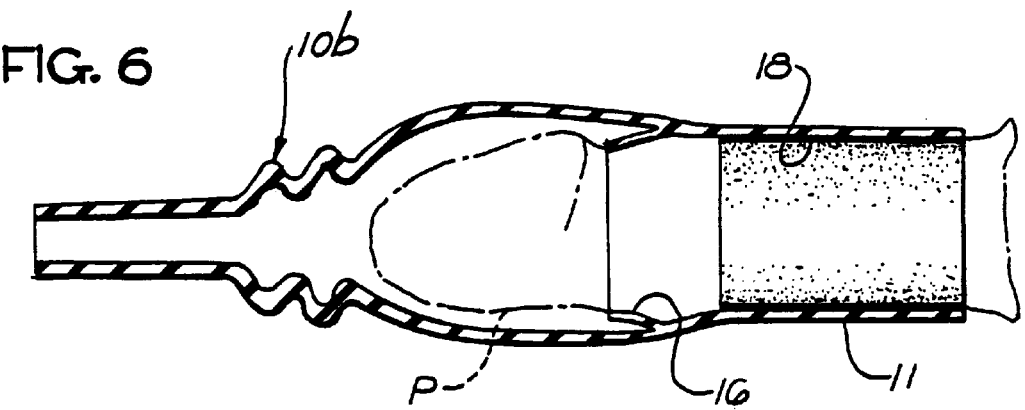

Since tube 20 has a larger inside diameter than the unstretched outside diameter of the sheath, the sheath is stretched slightly about the opening at end 20b and the cylindrical body section 11 is in a moderately tensioned state about the outer surface of the tube. Such stretching may cause the annular flap 16 to protrude outwardly away from the open end 20b of the tube as illustrated in FIG. 1. In any case, flap 16 can be easily viewed by the user at the time of application. Such application is commenced by first removing the protective release tape 22 and then urging the open end 20b of the applicator tube over the patient's penis P as depicted in FIG. 4. Flap 16 engages the glans (or the foreskin over the glans) and flexes inwardly. Continued advancement of the tube 20 brings the flap 16 to a position about the penile shaft directly behind the glans (FIG. 5). Thereafter, the user grips the exposed portion of the applicator tube near end 20a and pulls the drainage tube portion 13 of the catheter in a distal direction (away from the patient) while simultaneously urging the applicator tube 20 in a proximal direction (towards the patient) to cause the cylindrical body portion 11 to slide off of the applicator tube and onto the penile shaft. The applicator tube 20 and mesh sleeve 21 are then withdrawn, leaving the catheter in place upon the patient as illustrated in FIG. 6.

Effective sealing between annular flap 16 and the penile shaft occurs even though the flap is not highly stretched because the surface of the shaft is generally smooth and of even contour and because backflow, if it should occur, will tend to urge the flap into tighter sealing engagement with the penile shaft. It is to be understood, however, that the short annular flap 16 may be operative, although generally to a lesser extent, if it also engages the rear (proximal) portion of the glans—that is, if the catheter were applied with penile insertion into intermediate portion 12 no further than as shown in FIG. 4.

Figure 3:
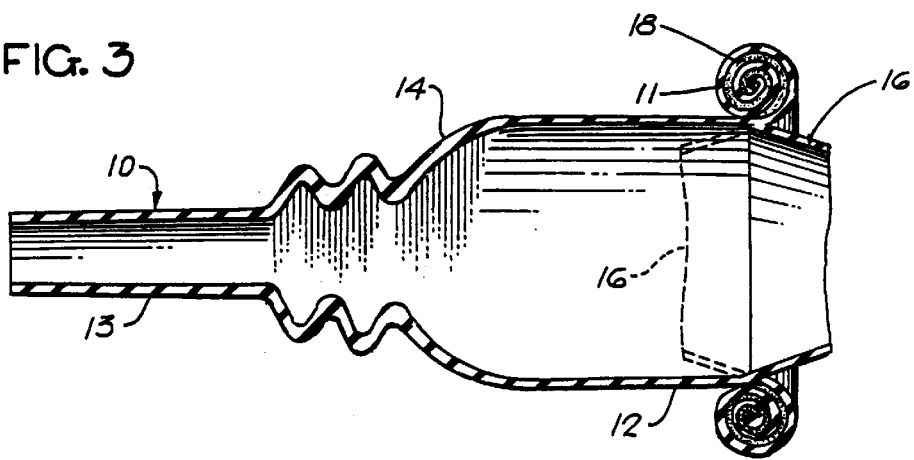
FIG. 3 is a sectional view of a catheter embodying the invention in rolled condition.

While the use of an applicator tube 20 is preferred, catheter 10 might instead be rolled in a conventional manner as illustrated in FIG. 3. In such a case, some means are necessary to prevent adhesive 18 from adhering to the outer surface (or what will become the outer surface) of the catheter. Such release means might take the form of a release tape or interliner (which in this case should be highly flexible) or of a release coating or release layer (e.g., of silicone rubber) applied to the outer surface of the catheter during manufacture. In all other respects, the catheter illustrated in FIG. 3 is identical to the catheter of FIG. 2.

While in the foregoing, we have disclosed embodiments of the invention in considerable detail for purposes of illustration, it will be understood by those skilled in the art that many of these details may be varied without departing from the spirit and scope of the invention.

We claim:

1. The combination of a male external catheter and applicator therefor; said catheter comprising a tubular sheath formed of soft elastic material having a thin-walled cylindrical portion for extending over the shaft of a patient's penis and having an adhesive coating along a portion of its inside surface, a reduced drainage tube portion, and an intermediate portion adapted to extend over and about a patient's glans and merging with both said drainage tube portion and said cylindrical portion; said sheath also including a thin, elastic, inwardly-extending annular flap having an outer end merging with said sheath between said cylindrical portion and said intermediate portion and having an inner end defining a generally circular opening; said applicator comprising a rigid and open-ended applicator tube; said intermediate portion of said sheath being located within said applicator tube and said drainage tube portion extending through and beyond the opening at one end of said applicator tube; said cylindrical portion of said sheath extending out of the opening at the opposite end of said applicator tube and extending along the outer surface of said applicator tube; and anti-friction means interposed between the outer surface of said applicator tube and said sheath; wherein the improvement comprises said opening at said inner end of said flap having a diameter of 75% to 92% of the inside diameter of said cylindrical portion, and a length within the range of 0.25 inches to 0.65 inches, when said flap and cylindrical portion are unstretched.

2. The combination of claim 1 in which said annular flap has an opening of about 78% to 89% of the inside diameter of said cylindrical portion.

3. The combination of claim 1 in which said flap has an opening diameter of about 81% to 87% of the inside diameter of said cylindrical portion.

4. The combination of claims 1, 2 or 3 in which said annular flap has a length no greater than 35% of the length of said intermediate portion.

* * * * *